United States Patent [19]
Fleming et al.

[11] Patent Number: 6,060,643
[45] Date of Patent: May 9, 2000

[54] MOUSE MODEL WITH HUMAN IMMUNE SYSTEM

[75] Inventors: William H. Fleming; Edmund K. Waller, both of Atlanta; Curtis W. Turner, Marietta, all of Ga.

[73] Assignee: Emory University, Atlanta, Ga.

[21] Appl. No.: 08/511,396

[22] Filed: Aug. 4, 1995

[51] Int. Cl.$^7$ ............................ C12N 15/00; A61K 35/00
[52] U.S. Cl. ................................. 800/8; 800/11; 424/9.1; 424/9.2; 424/93.1; 424/534; 424/529
[58] Field of Search .................. 800/2, 8, 11; 425/172.3; 424/9.1, 9.2, 529, 534, 93.21

[56] References Cited

U.S. PATENT DOCUMENTS

| | | | |
|---|---|---|---|
| 5,639,939 | 6/1997 | McCune | 800/2 |
| 5,652,373 | 7/1997 | Reisner | 800/2 |

OTHER PUBLICATIONS

Murphy et al. (1992) Eur. J. Immunol., vol. 22, 1421–1427, 1992.
Nolta et al. "Sustained Human Hematopoiesis in Immunodeficient Mice by Contransplantation of Marrow Stroma Expressing . . . " *Blood* 83(10):3041–3051, May 15, 1994.
Baum et al. "Isolation of a Candidate Human Hematopietic Stem–Cell Population" *Pro. Natl. Acad. Sci. USA* 89:2804–2808, Apr. 1992.
Lapidot et al. "Cytokine Stimulation of Multilineage Hematopoiesis from Immature Human Cells Engrafted in SCID Mice" *Science* 255:1137–1141, Feb. 28, 1992.
Mosier et al. "Human Immunodeficiency Virus Infection of Human–PBL–SCID Mice" *Science* 251:791–794, Feb. 15, 1991.
Namikawa et al. "Infection of the SCID–hu Mouse by HIV–1" *Science* 242:1684–1686, Dec. 23, 1988.
McCune et al. "The SCID–hu Mouse: Murine Model for the Analysis of Human Hematolymphoid Differentiation and Function" *Science* 2:4:1632–1639, Sep. 23, 1988.
Mosier et al. "Transfer of a Functional Human Immune System to MIce with Severe Combined Immunodeficiency" *Nature* (London) 335:256–259, Sep. 15, 1988.
Mead et al Biotechnology therapeutics 4(1+2): 137, 1993.
Meyer et al Advances in Immunology 56: 303, 1991.
Van Keogh et al Journal of Immunol 153(10): 4826, 1994.
Bankers et al Current Trans in Microb & Immunol 152: 201, 1989.
McCure et al Science 241 : 1632, 1980.
Torlert et al., Immunol. Reviews 124 :139, 1991.

*Primary Examiner*—Deborah Crouch
*Assistant Examiner*—Anne Marie S. Beckerleg
*Attorney, Agent, or Firm*—Needle & Rosenberg, P.C.

[57] ABSTRACT

The present invention provides a non-human genetically immunodeficient mammal the peripheral blood of which contains a non-lethal percent of T-cells of human origin which is at least 20% as well as a non-human genetically immunodeficient mammal having a lethal percent of T-cells of human origin in the peripheral blood which is at least 60%. Also provided is a method of screening a substance for anti-HIV activity comprising obtaining a non-human genetically immunodeficient mammal having a lethal percent of human T-cells in the peripheral blood which is at least 60%; infecting the mammal with an amount of HIV sufficient to rescue the mammal from death from the effects of the lethal percent of human T-cells; administering the substance to the mammal; and determining if the substance kills the mammal by inhibiting the rescue of the mammal by HIV, the death of the mammal indicating a substance having anti-HIV activity.

27 Claims, 1 Drawing Sheet

MOUSE MODEL WITH HUMAN IMMUNE SYSTEM

This invention was made in part with government support under Grants No. HL52965-01, NS24097 and CA40282 from the National Institutes of Health. The government has certain rights in this invention.

BACKGROUND OF THE INVENTION

1. Filed of the Invention

The present invention relates to a genetically immunodeficient nonhuman mammal with a human immune system. In particular, the present invention relates to a genetically immunodeficient mouse having human T-cells within its hematopoietic system, methods for producing these mice and methods for using this mouse model to assay for inhibitors of human immunodeficiency virus (HIV) infection and to assay substances for their effects on human T-cells.

2. Background Art

Progress in the development of drugs which alter immune system function or protect against retroviral infection have been impeded by the absence of a suitable in vivo model system of T-cell development. The requirement for the appropriate hematopoietic microenvironment complete with the requisite cytokines has in part been met by the SCID-hu mouse model system (Baum, C. M., et al. 1992. *Proc. Natl. Acad. Sci. USA* 89:2804–2808; McCune, J. M., et al. 1988. *Science* 241:1632–1639). SCID-hu mice contain grafts of fetal thymus, liver and bone marrow, which permit the development of human B-cells, T-cells and myeloid cells. Intraperitoneal injections of human peripheral blood have produced lymphoid engraftment in SCID mice although both the frequency and duration of engraftment have been low (Mosier, D. et al. 1988. *Nature* (London) 335:256–259). To circumvent these difficulties, SCID mice have been treated with injections of human progenitor cells and a cocktail of human cytokines. The use of exogenous cytokines in this setting modestly improves the frequency and extent of engraftment (Lapidot, T., et al. 1992. *Science* 255:1137–1140; Nolta, J. A., et al. 1994 *Blood* 83:3041). This finding is consistent with the observation that many murine growth factors are thought to have reduced activity on human progenitor cell populations. Human T-cells transplanted into immunodeficient mice have been demonstrated to be infectable with human immunodeficiency virus-1 (HIV-1) Namikawa, R., et al. 1988. *Science* 242:1684–1686; Mosier, D. E., et al. 1991. *Science* 251:791–794). The low percentage of human T-cells found in the peripheral blood, spleen and bone marrow of these recipient mice remains a major limitation to studying the effects of agents which may inhibit HIV-1 replication and infection. In summary, low levels of human T-cell engraftment and the absence of an unambiguous endpoint for evaluating the antiviral activity of specific agents significantly limits the utility of the current in vivo model systems for T-cell function. Thus, there remains a need for an in vivo model for human T-cell function in which greater levels of T-cell engraftment can be established for the purpose of developing reliable and reproducible assays to antiviral activity and the effects of various agents on human T-cell function.

The present invention satisfies this need by providing a genetically immunodeficient mammal having large numbers of T-cells of human origin in its hematopoietic system. The present invention also provides a method for generating these animal models and methods for using these animals in assays to screen for compounds with anti-HIV activity and to screen substances for their effects on human T-cells.

SUMMARY OF THE INVENTION

Figure 1:
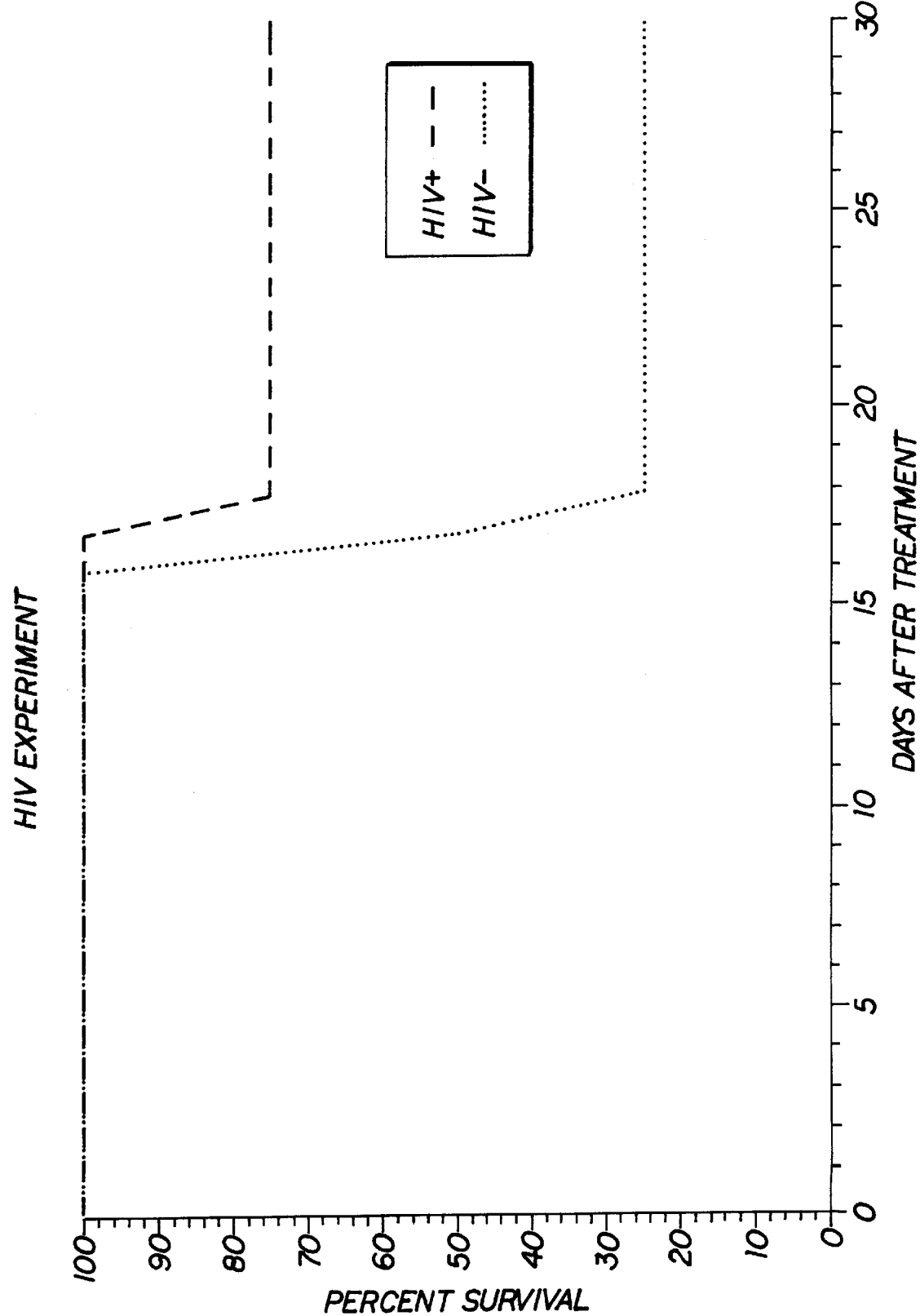
FIG. 1 shows the effect of HIV infection on the survival of mice having a lethal percent of human T-cells in their peripheral blood. Approximately 75% of BNX-hu chimeras having a lethal percent of human T-cells in their peripheral blood failed to survive up to 30 days after human peripheral blood mononuclear cell (PBMC) administration, in the absence of infection with LAI, a laboratory strain of HIV. BNX-hu chimeras having a lethal percent of human T-cells in their peripheral blood that were injected with 500 i.u. of LAI demonstrated a survival rate of 75–80% at 30 days after PBMC administration.

The present invention provides a non-human genetically immunodeficient mammal the peripheral blood of which contains at least 10% T-cells of human origin.

The present invention also provides a nonhuman genetically immunodeficient mammal having a percent of T-cells of human origin in the peripheral blood which is lethal to the mammal.

The present invention further provides a method of screening a substance for anti-HIV activity comprising obtaining a non-human genetically immunodeficient mammal having a lethal percent of human T-cells in the peripheral blood; infecting the mammal with an amount of human immunodeficiency virus sufficient to rescue the mammal from death from the effects of the lethal percent of human T-cells; administering the substance to the mammal; and determining if the substance kills the mammal by inhibiting the rescue of the mammal by human immunodeficiency virus; the death of the mammal indicating a substance having anti-human immunodeficiency virus activity.

Also provided is a method of making a non-human mammalian model for screening a substance for its effect on HIV infection of human cells comprising providing a non-human genetically immunodeficient mammal; administering to the mammal a dose of radiation sufficient to establish a lethal percent of T-cells of human origin into the peripheral blood of the mammal; and transplanting into the mammal an amount of human T-cells sufficient to establish a lethal percent of T-cells of human origin in the mammal.

The present invention also provides a method of making a non-human mammalian model for screening a substance for its effect on human T-cells, comprising providing a non-human genetically immunodeficient mammal; irradiating the mammal at a dose sufficient to establish at least 10% T-cells of human origin in the peripheral blood of the mammal; and transplanting into the mammal an amount of human T-cells sufficient to establish at least 10% T-cells of human origin in the peripheral blood of the mammal.

Furthermore, the present invention provides a method of screening a substance for its effect on human T-cells, comprising obtaining a non-human genetically immunodeficient mammal the peripheral blood of which contains at least 10% T-cells of human origin; administering the substance to the mammal; and observing the effect of the substance on the human T-cells of the mammal.

Various other objectives and advantages of the present invention will become apparent from the following description.

DESCRIPTION OF THE PREFERRED EMBODIMENTS

The present invention may be understood more readily by reference to the following detailed description of specific embodiments and the Examples included herein. As used herein, "a" can mean one or more, depending on the context in which it is used.

This invention provides a non-human genetically immunodeficient mammal the peripheral blood of which contains at least 10% T-cells of human origin. The invention also provides such a mammal having at least 20%, 30%, 40%, 50%, 60%, 70%, 80%, 90%, up to 100% T-cells of human origin in the peripheral blood of the mammal. Also provided are ranges of these percentages including, for example, 30% to 60%, 30% to 40%, 30% to 50%, 40%–60%, etc.

When the percentage of human T-cells reaches about 60% or greater, the T-cells can be lethal to the mammal. When the T-cells are 70% to 90% or 100%, especially 80% to 90% or 100%, the T-cells are typically lethal to the animal. "Lethal percent of T-cells" as used herein means an amount of T-cells which will kill a significant number of mammals relative to a control within a defined period of time that is shorter than the mammal's natural lifespan, e.g. 25% survival at 30 days after human T-cell administration.

The mammal can be any mammal which is non-human. Typically, small mammals such as mice will be preferred, due to costs and availability. Other mammals include, for example, rats, hamsters, guinea pigs, rabbits, dogs, cats, goats and non-human primates.

The mammal is typically genetically immunodeficient. An immunodeficient mammal is important for this invention because such animals are incapable of rejecting the transplanted human immune cells due to a defect in, but not necessarily limited to, B-cells, T-cells and natural killer (NK) cells. One such mammal is the beige/nude/xid mouse which has three separate mutations resulting in a defect in the animal's ability to produce T-cells, B-cells and NK cells. Other mammals which could be utilized include virtually any mammalian species in which mutations, resulting in phenotypes such as those known in the art as SCID, NOD, nude, xid, and/or beige, spontaneously occur. Alternatively, these mutations may be genetically engineered in any number of species.

These mammals are valuable for screening a substance for its effect on human T-cells. A "substance" as used herein includes, for example, compounds, peptides, cytokines, antibodies, proteins, pharmaceuticals, infectious agents such as viruses and bacteria, and the like. Thus, the subject mammals infected with various agents that affect T-cells, e.g., HIV and human T-cell leukemia/lymphoma virus-I (HTLV-1) are also provided.

The substances can be administered orally, intravenously, intramuscularly, intraperitoneally, rectally or by any other route to introduce the substance into the body of the mammal. One of ordinary skill in the art would be able to determine the best route of administration, on the basis of the nature of the substance to be tested, knowledge of use of the substance in other applications and the effect on T-cells to be evaluated. Such T-cell effects can include but are not limited to cell death, cell proliferation, release of various substances from the T-cells and the like.

The method of this invention can also be used to screen for other infectious agents which are now known or may be discovered in the future to kill, inhibit, or affect the function of human T-cells. For example, such infectious agents may include HIV, HTLV-1 and other members of the Retroviridae family.

The invention also provides a method of making a non-human mammalian model for screening a substance for its effect on HIV infection of human cells comprising providing a non-human genetically immunodeficient mammal; administering to the mammal a dose of radiation sufficient to establish a lethal percent of T-cells of human origin; and transplanting into the mammal an amount of human T-cells sufficient to establish a lethal percent of T-cells of human origin in the peripheral blood of the mammal.

The invention also provides a method of making a non-human mammalian model for screening a substance for its effect on human T-cells, comprising providing a non-human genetically immunodeficient mammal; irradiating the mammal at a dose sufficient to establish at least 10% T-cells of human origin in the mouse; and transplanting into the mammal an amount of human T-cells sufficient to establish at least 10% T-cells of human origin in the peripheral blood of the mammal.

Human T-cells suitable for transplantation in this invention can be obtained by a variety of methods, e.g., apheresis, which entails separating PBMC from the other formed elements of the blood by a centrifugation process. Typically, 20 liters of blood from a donor are processed during the procedure (*Current Status of Hemapheresis: Indications, Technology and Complications Technical Workshop.* 1987. Westphal, R. G. & Kasprisin, D. O., American Association of Blood Banks, Arlington, Va.). Removal of blood from a peripheral vein and separation of PBMC by centrifugation may also be employed (Mosier et al.). The T-cells can then be purified from the population of PBMC with affinity chromatography, by passing the cells over a column containing mouse-anti-human CD3 antibodies and recovering the bound CD3+ cell fraction. CD3 is an antigen present on the surfaces of all types of human T-cells, therefore, selection of cells possessing this surface marker will produce a purified population of human T-cells.

Examples of immunodeficient mammals have been set forth above. The amount of radiation and the number of humanT-cells administered to the mammal depends on the species, size and condition of the mammal and its susceptibility to radiation. On the basis of data available in the literature, a skilled artisan would be able to determine the maximum sublethal dose for any mammal which could be employed in this invention. For example, a SCID mouse cannot tolerate as much radiation as the beige/nude/xid mouse. Thus, the amount of radiation would have to be lowered for a SCID mouse. Likewise, because the radiation dose is lower, the engraftment of the human T-cells will be lower. Thus, at a lower radiation dose it is necessary to increase the amount of human T-cells administered to the mammal. The number of human T-cells administered to a mouse with an average weight of 20 grams to obtain the desired level of engraftment to ultimately establish the desired percentage of human T-cells in the peripheral blood, is typically between about $1\times10^7$ and $1\times10^8$ cells, which is a dose of about $1\times10^7$ to $1\times10^8$ cells/20 grams of body weight or approximately $5\times10^8$ to $5\times10^9$ cells/kilogram of body weight. This latter value can be used in determining the number of cells to administer to other mammalian species, of various sizes and radiation susceptiblity, which can be employed in this invention. However, these amounts can be varied depending on the dosage of radiation administered to the mammal and the desired percent of human T-cells in the mammal.

The radiation dose for mice is typically between 400 and 1100 rads, including at least 400, 500, 600, 700, 800, 900, 1000 and 1100 rads. "At least" as used herein excludes radiation dosages on the high end which are lethal to the mammal such that a human T-cell population cannot be established for a useful period of time before death of the mammal. Also included are ranges of these dosages, e.g., 700 to 1100 rads, 500 to 600 rads, 600 to 800 rads, etc. However, these dosages can be varied depending on the number of human T-cells administered and the desired percent of human T-cells in the mammal. For example, a 700 rad dose can provide 90% engraftment of human peripheral blood mononuclear cells, resulting in about 75% human T-cells in the peripheral blood of the mammal. Likewise, a 400 rad dose can result in 18% engraftment of human peripheral blood mononuclear cells, resulting in 35% human T-cells in the peripheral blood of the mammal. Moreover, the invention provides radiation doses for other mammals which produce engraftment equivalent to that produced by these radiation doses in mice.

Typically, if a dose of radiation is so high as to be lethal to the mammal and therefore not useful in screening methods, the dose can be split to allow for a better engraftment without being lethal. Preferably, at least three hours between irradiations is utilized. For example, if a 700 rad dosage is desired to obtain a percentage of human T-cells in a mouse greater than 50%, the 700 rad dosage is preferably split into two 350 rad dosages at least three hours apart and preferably between three and four hours apart. Longer time periods between irradiations can be routinely optimized, using the methods set forth in the Examples.

The dosage of radiation is important to establish levels of human T-cells greater than 50% in the peripheral blood of the mammal. For example, the dosage to establish greater than 50% human T-cells in the peripheral blood of a mouse is between 700 and 1100 rads. Such dosages allow one to establish a percentage of human T-cells in the peripheral blood of the mammal approaching 100%. As noted above, such high levels of human T-cells can be lethal to the mammal. However, this invention provides a screening method which effectively utilizes the lethality of such high human T-cell levels.

Specifically, the invention provides a method of screening a substance for anti-HIV activity comprising obtaining a non-human genetically immunodeficient mammal having a lethal percent of human T-cells in the peripheral blood; infecting the mammal with an amount of HIV sufficient to rescue the mammal from death from the effects of the lethal percent of human T-cells; administering the substance to the mammal; and determining if the substance kills the animal by inhibiting the rescue of the mammal by HIV; the death of the mammal indicating a substance having anti-HIV activity. The phrase "by inhibiting the rescue of the mammal by HIV" as used herein means that the infection of human T-cells in the mammal with HIV typically results in a reduction of the number of human T-cells in the mammal to a percent that is not lethal to the mammal and a substance with anti-HIV activity will reverse the effect of the HIV infection on human T cells in the mammal, resulting in an increase in the percent of human T-cells in the peripheral blood to a lethal level, typically within about 30 days after administration of the human T-cells. However, the time period to lethality will vary depending on the level of anti-HIV activity.

As noted above, the percent of human T-cells established in the peripheral blood of the mammal depends on the radiation dosage and the number of human T-cells administered. For the method of screening substances for anti-HIV activity, it is critical to establish a percent of human T-cells in the peripheral blood of the mammal which is lethal to the mammal. Typically, human T-cells are lethal over weeks or months but, depending on the research goal, the lethality could be over years, e.g., to more readily duplicate acquired immunodeficiency syndrome (AIDS) in humans. All of these parameters can be varied to generate a mammal with the desired period to death resulting from the establishment of human T-cells in the mammal's peripheral blood.

The invention also provides a more general method of screening a substance for its effect on human T-cells, comprising obtaining a non-human genetically immunodeficient mammal the peripheral blood of which contains at least 10% T-cells of human origin; administering the substance to the mammal; and observing the effect of the substance on the human T-cells of the mammal. Such a method typically would not require such a high dose of radiation so as to make the human T-cell number lethal to the mammal. However, the methods set forth above of generating a suitable mammal which can be used in screening could be utilized to generate mammals having greater than 20%, 30%, 40%, 50%, 60%, 70%, 80%, 90% up to about 100% human T-cells in the peripheral blood.

Examples of applications of this method including screening substances for their effects on disorders of cell mediated immunity and diseases involving T-cell dysfunction. For example, the method of the present invention can be employed to evaluate agents which may modulate autoimmune diseases such as rheumatoid arthritis in mice that have been implanted with joint tissues and the immune cells from patients with this disease. Other applications can include evaluation of agents that modulate the interaction between the host's T-cell compartment and host tissues which are involved in the autoimmune process in, for example, systemic lupus erythematosus and Type 1 diabetes.

The present invention is more particularly described in the following examples which are intended as illustrative only since numerous modifications and variations therein will be apparent to those skilled in the art.

EXAMPLES

Example I

Generation of BNX-hu Chimeras.

Mice. Eight week old homozygous beige nude xid (BNX) mice (Harlen Sprague Dawley, Indianapolis, IN) were used as recipients. Animals were housed in sterile microisolator cages and maintained on acidified water (pH 2.2) in the animal care facility at Emory University, Atlanta, Ga.

Human hematopoietic cells. Tissue sources of human hematopoietic progenitor cells (HPC) were obtained with informed consent and the approval of the Human Investigations Committee at Emory University. Fetal bone marrow cells (FBM) were harvested from the femurs and tibias of 16–20 week old fetuses obtained from Advanced Bioscience Resources, Inc. (Alameda, Calif.). Single cell suspensions of FBM were prepared by flushing the bone marrow out of the femurs and tibias into RPMI medium with 3% bovine serum albumin. Adult bone marrow cells (ABM) and granulocyte colony stimulating factor (G-CSF) -mobilized PBMC were obtained from allogeneic donors from the Bone Marrow Transplant Program at Emory University. The PBMC were collected by apheresis. For flow cytometry, normal human peripheral blood cells were obtained as a positive control from platelet pheresis volunteers. Erythrocytes were depleted from samples using 3% T-500 Dextran followed by hypotonic saline lysis. CD34+ Cell Purification. Cells were washed with HBSS supplemented with 1% bovine serum albumin and incubated with a biotinylated CD34 monoclonal antibody (12.8; Cell Pro, Inc., Bothell, Wash.). The cells were passed over a CEPRATE LC34 Column (Cell Pro, Inc., Bothell, Wash.) and the bound CD34+ cell fraction was recovered. These enriched CD34+ cells were then assayed for colony forming activity and engraftment in the BNX mice.

CD3+ Cell Purification. Cells can be washed with HBSS supplemented with 1% bovine serum albumin and passed over an affinity chromatography column containing mouse-anti-human CD3 antibodies and the bound CD3+ cell fraction recovered.

Methylcellulose Assays. Cells obtained from PBMC, ABM or FBM were cultured in triplicate in Iscove's methlycellulose Ready-Mix supplemented with erythropoietin and 50 $\mu$l. of phytohemagglutinin-stimulated conditioned medium and 1% fetal bovine serum (Terry Fox Lab, Vancouver, BC). Plates were incubated at 37° C. and 5% $CO_2$ for 14 days and colony forming units of granulocyte/macrophage (CFU-GM) colonies were scored on an inverted microscope.

Transplantation of human cells into BNX mice. Mice received either a single dose of 400 rads or 700 rads split into two 350 rads doses given three hours apart using a Gamma Cell 40 irradiator (Atomic Energy, Ottawa, Canada) at a dose rate of 100 rads/min. Human cells, at a final concentration of 1.5 to $2.0\times10^8$ cells/mnl in a volume of 500 ml of HBSS/10 mM Hepes/3% FCS, were injected into the retro-orbital sinus while the mice was under methoxyflurane anesthesia. Post-transplantation, recipient mice were maintained on aqueous antibiotics (neomycin sulfate 1.1 g/L and polymyxin B 167 mg/L) for four weeks. Mice were analyzed for engraftment of human cells at two time points. The peripheral blood was analyzed at 6–8 weeks after transplantation. At six months, mice were sacrificed and analyzed for the presence of human cells in the peripheral blood, bone marrow and spleen.

Phenotypic and functional characteristics of transplanted cells. Three different sources of human hematopoietic cells (PBMC, ABM and FBM) were immunophenotyped to enumerate the dose of progenitor cells (CD34+) and T lymphocytes (CD3+) in the transplantation population (Table 1). Although the mean nucleated cell dose for each cell source was similar, (ranging from 75 to $95\times10^6$ cells/animal), the mean CD34+ cell dose varied substantially. FBM contained $16\times10^6$ CD34+ cells while PBMC and ABM contained $0.9\times10^6$ and $1.7\times10^6$ cells, respectively (Table 1). In contrast, the CD3+ cell dose of the PBMC was $36\times10^6$, 3.8 fold higher than that of ABM and at least 50 fold higher than FBM. To determine the functional characteristics of these different hematopoietic cell sources, committed progenitor activity was evaluated using methylcellulose assays. The PBMC, ABM and FBM sources contained similar numbers of CFU-GM colony forming units with the infused dose ranging from 6.3 to $7.8\times10^4$ cells/animal (Table 1). Although the total nucleated cell dose and number of committed progenitor cells in these three cell sources were similar, the CD34+ cell and CD3+ cell doses varied substantially (Table 1).

Example II

Analysis of Human Cells Engrafted into BNX-hu Chimeras.

Flow cytometric analysis of human cells in BNX mice. Mice were anesthetized at 6–8 weeks post-transplant with methoxyflurane and 200 $\mu$l of peripheral blood was obtained from the retro-orbital sinus. Red cells were depleted using T-500 Dextran sedimentation and hypotonic lysis. Spleen and bone marrow were harvested from euthanized mice. Spleens were mechanically disrupted and bone marrow cells were prepared by flushing the femurs and tibias from each mouse. The cells suspensions were passed over a nylon filter to remove connective tissue. Engraftment of human myeloid cells (CD13,33), B-cells (CD19) and T-cells (CD3; CD4; CD8) were determined by flow cytometry on a FACScan (Becton Dickinson, Mountain View, Calif.). Monoclonal antibodies directed against lineage specific epitopes were purchased from Becton Dickinson (Sunnyvale, Calif.). Antibodies to the $\alpha$V2 and $\beta$V chains of the human T cell receptor (TCR) were purchased from T Cell Sciences (Cambridge, Mass.). Bone marrow, peripheral blood and spleen cells were suspended in Hank's balanced salt solution (HBSS)/10 mM Hepes/3% fetal calf serum (FCS), blocked with normal mouse serum and incubated at 40° C. for 20 minutes with directly conjugated antibodies. After washing and centrifugation, the cells were suspended in HBSS/10 mM Hepes/3% FCS containing 1 $\mu$g/ml propidium iodide (PI). Non-viable cells and red cells were excluded using forward scatter, side scatter or PI staining. The monoclonal antibodies used to detect human cells in the BNX mice were all human specific. In all experiments, human and BNX mouse cells served as positive and negative controls, respectively. Nonspecific binding was also evaluated using isotype controls. For each sample, 10,000 to 50,000 events were analyzed to a sensitivity for the detection of human cells of at least 0.2%.

High levels of human cells are present in the peripheral blood of BNX mice transplanted with human PBMC. To evaluate the percentage of human cells present in the circulation of recipient BNX mice 6–8 weeks post-transplant, peripheral blood was analyzed using monoclonal antibodies directed against the human CD45 epitope. Recipient mice were considered to be chimeric if they had $\geq$1% human CD45+ cells in the peripheral blood. Ten of 57 (17.5%) mice injected with PBMC were chimeric. Substantial variability in the level of circulating human cells was observed; the percentage of CD45+ cells ranged from 1 to 94% (mean= 41%). In contrast, injection of ABM led to engraftment in only two of 42 animals (4.7%) and the percentage of human cells in the peripheral blood of these two recipients was 10.8% and 1.1%, respectively. Although the FBM had the highest content of CD34+ cells, none of 25 animals given FBM had human cells in the peripheral blood at 6–8 weeks post-transplant.

BNX recipients of human peripheral blood mononuclear cells engraft with human CD3+ cells. To define the specific lineages of human cells in the peripheral blood of recipient mice 6–8 weeks post-transplant, three color flow cytometry was performed using human specific monoclonal antibodies directed against T cells (CD3), B-cells (CD19) and myelomonocytic cells (CD13/33). The CD45+ human cells in the peripheral blood of recipient mice consistently coexpressed the pan-T-cell marker, CD3. These cells did not express CD19 or CD13/33. These results indicate that up to two months after transplantation, the human cells in the circulation of these chimeric mice are exclusively T-cells.

Human CD3+ cells engrafted in BNX mice are polyclonal. To evaluate whether the engrafted T cells in recipient mice were derived from the expansion of a specific T-cell subset, the expression of CD4, CD8 and the variable usage of the TCR $\alpha$ and $\beta$ genes was analyzed. Analysis of spleen cells of a representative chimeric mouse showed 38% human CD3+ cells. Of these cells, 18% were CD8+, 19% were CD4+ and less than one percent expressed both CD4 and CD8. Gated human CD3+ cells were analyzed to determine the frequency of TCR gene expression. The $\alpha$V2 chain was expressed on only 2.9% of the CD3+ cells. Variable expression of several $\beta$V subunits was observed. The percentage of CD3+ cells expressing specific $\beta$ gene rearrangements were as follows: $\beta$V5c (3.6%), $\beta$V6a (1.9%), βV8a (4.0%) and βV12a (1.2%). These results indicate polyclonal expansion of T-cells in BNX recipients and a pattern of βV gene expression consistent with that observed in normal human T-cell populations.

The short-term engraftment of human CD3+ cells is dose dependent. Significant variation existed in the CD3+ cell dose in PBMC ($36\times10^6$), ABM ($9.5\times10^6$) and FBM ($<0.7\times10^6$). There was a direct correlation between the number of CD3+ cells injected and the percentage of CD3+ cells in the peripheral blood of chimeric recipients 6–8 weeks after transplantation (r=0.99). This dose dependence did not correlate with long-term engraftment in BNX recipients of PBMC; only one of 35 mice studied at six months post-transplant demonstrated human CD3+ cells in the spleen or bone marrow (Table 2).

Long-term multilineage human hematopoiesis in BNX mice. To determine whether PBMC, ABM or FBM could give rise to long-term human hematopoiesis in mice, the peripheral blood, bone marrow and spleen of recipient animals were examined six months after transplant. One of 35 (2.8%) mice transplanted with PBMC demonstrated chimerism at six months. Although human cells were not detected in the peripheral blood of this recipient, the spleen and bone marrow contained 32% and 1.6% CD45+ cells, respectively. These CD45+ cells coexpressed CD3, but other lineage markers were not detected. Similarly, only one of 38 mice (2.6%) receiving ABM demonstrated chimerism at six months and engraftment was restricted to the bone marrow, which contained 18.3% CD45+ cells. However, in contrast to the findings in PBMC recipients, multilineage hematopoiesis was present in these ABM recipients and the CD45+ cells coexpressed CD34 (16%), CD19 (66%) or CD 13/33 (14%). Also, unlike long-term PBMC recipients, CD3+ cells were not detected in long-term ABM recipients.

Four of 26 mice (15%) injected with FBM were chimeric six months post-transplant (Table 2). The peripheral blood in two of four chimeric mice contained 1% human B cells (CD45/CD19). The level of engraftment of CD45+ cells in the bone marrow and spleen of FBM recipients ranged from 3.9% to 73%. Myelomonocytic markers (CD13,33) were present on 1% to 19% of cells and CD19 was detected on 2.4% to 48% of the cells in the BNX bone marrow. Sixteen to 22% (mean=20%) of these CD45+ cells coexpressed CD34. The expression of CD3+ cells was not detected in the peripheral blood, bone marrow or spleen of the chimeric FBM recipients. These results demonstrate that both ABM and FBM can give rise to long-term hematopoietic reconstitution in BNX mice transplanted while PBMC produces both short-term and long-term engraftment that is nevertheless restricted to the T-cell lineage.

Engraftment of BNX mice with human cells is not donor specific. The frequency of engraftment of human cells in recipient BNX mice was evaluated with respect to the characteristics of individual donors (Table 3). Seventeen percent of the PBMC recipients were chimeric and were derived from five of ten PBMC donors. When individual PBMC donors were examined, the number of chimeric mice per donor averaged 25%. Similarly, three of 11 ABM donors gave rise to only three chimeric mice. In contrast, four of five FBM donors gave rise to four long-term chimeric mice with an average engraftment frequency of 25%. These results indicate that the engraftment frequencies observed with PBMC, ABM or FBM are not simply due to high levels of engraftment of cells from specific donors.

In summary, the CD34+ cell dose was highest in the FBM recipients, which had the highest rates of long-term chimerism. The CFU-GM dose was comparable between the different stem cells sources but did not predict long-term chimerism. The CD3+ cell dose was lowest in the FBM recipients, which had the highest rates of human stem cell engraftment in the long-term experiments.

Example III

Screening Substances for Anti-HIV Activity.

Infection of BNX-hu chimeras with human immunodeficiency virus (HIV). BNX mice were irradiated with two doses of 350 rads separated by a three hour interval, for a total dose of irradiation of 700 rads. The mice were injected intravenously with $1\times10^8$ PBMC collected from donors by apheresis. The mice were then injected 24–48 hours later intravenously with 500 infectious units (i.u.) of the laboratory strain of HIV designated LAI. The mice were maintained on antibiotic water and monitored daily for survival. As shown in FIG. 1, animals that received PBMC alone demonstrated an average survival rate of 25% at 30 days after administration of the cells, indicating that a lethal percent of T-cells was established in the peripheral blood of these mice. Mice that were injected with PBMC and subsequently injected with LAI demonstrated an average survival rate of 75–80% at 30 days after administration of the PBMC. Thus, infection by HIV prolonged survival of mice that had established lethal percentages of human T-cells, presumably by reducing the percent of human T-cells in the peripheral blood of mice to sub-lethal levels.

Screening substances for anti-HIV activity. BNX mice can be irradiated with two doses of 350 rads separated by a three hour interval, for a total irradiation dose of 700 rads. The mice can then be injected intravenously with $1\times10^8$ PBMC collected from human donors by apheresis or $1\times10^8$ purified human CD3+ cells. The mice can then be injected 24–48 hours later intravenously with 500 i.u. of the laboratory strain of HIV designated LAI. The substance can then be administered to the mice. The mice can then be maintained on antibiotic water and monitored daily for survival. If the survival rate of the mice is 75% or greater at 30 days after PBMC administration, the substance would be considered not to have anti-HIV activity. If the survival rate of the mice is less than 70% at 30 days after human T-cell administration, the substance would be considered to have anti-HIV activity.

Example IV

Determining the Effect of a Substance on Human T-cells.

Screening substances for their effects on human T-cells BNX mice can be irradiated with between 400 and 1100 rads and injected intravenously with $1\times10^8$ PBMC collected from human donors by apheresis or $1\times10^8$ purified human T-cells to generate a BNX-hu chimera having at least 10% T-cells of human origin in the peripheral blood. A substance can then be administered to the mice and the effect of that substance on the human T-cells in the peripheral blood of the mice can be determined.

Throughout this application, various publications are referenced. The disclosures of these publications in their entireties are hereby incorporated by reference into this application in order to more fully describe the state of the art to which this invention pertains.

Although the present invention has been described with reference to specific details of certain embodiments thereof, it is not intended that such details should be regarded as limitations upon the scope of the invention except as and to the extent that they are included in the accompanying claims.

TABLE 1

Engraftment of the Peripheral Blood of BNX Mice at 6–8 Weeks Post Transplant

| Cell Source | Input Cells | | | | Transplant Outcome | | |
|---|---|---|---|---|---|---|---|
| | Nucleated × $10^6$ | CD34+ × $10^6$ | CD3+ × $10^6$ | CFU-GM × $10^4$ | Recipient Mice | Chimeric Mice | (%) |
| PBMC | 95 ± 16 | 0.9 ± 1.0 | 36 ± 13 | 6.3 ± 1.1 | 57 | 10 | (17.5) |
| ABM | 89 ± 40 | 1.7 ± 0.9 | 9.5 ± 3.9 | 6.4 ± 3.4 | 42 | 2 | (4.7) |
| FBM | 75 ± 44 | 16 ± 3.2 | <0.7* | 7.8 ± 4.7 | 25 | 0 | (0) |

*The limit of detection is 0.2%. Chimerism was defined as 1% or greater human CD45+ cells being present in the peripheral blood. Abbreviations: PBMC, peripheral blood mononuclear cells (N = 10); ABM, adult bone marrow (N = 11); FBM, fetal bone marrow (N = 5). The mean ± SD is shown.

TABLE 2

Phenotypic Analysis of BNX-hu Chimeras Six Months Post Transplant

| Mouse # | Input Cells | % Human Cells in BNX | | | | | | | | | |
|---|---|---|---|---|---|---|---|---|---|---|---|
| | | Marrow CD | | | | | Spleen CD | | | | |
| | | 45 | 3 | 19 | 34 | 13/33 | 45 | 3 | 19 | 34 | 13/33 |
| 1 | FBM* | 73 | — | 48 | 16 | 19 | 0.2 | — | — | — | — |
| 2 | FBM | 12.5 | — | 8.9 | 3.0 | 4.1 | — | — | — | — | — |
| 3 | FBM | 4.9 | — | 2.4 | 0.8 | 1 | — | — | — | — | — |
| 4 | FBM | — | — | — | — | — | 3.9 | — | 3.3 | — | — |
| 5 | ABM* | 18.3 | — | 12 | 3.0 | 2.6 | — | — | — | — | — |
| 6 | PBMC | 1.6 | 1.6 | — | — | — | 32 | 32 | — | — | — |

*Indicates purified CD34+ cells obtained from these samples. Percentage of human cells indicates percentage of total nucleated cells positive for the respective cell surface markers. Level of detection is ≧ 0.2%.

TABLE 3

Engraftment of BNX mice is not donor dependent.

| Donor # | Input Cells | Chimeric/Injected | Weeks Engrafted | Tissues Engrafted |
|---|---|---|---|---|
| 1 | PBMC | 3/10 | 7 | PB |
| 2 | PBMC | 2/10 | 6 | PB |
| 3 | PBMC | 1/11 | 6 | PB |
| 4 | PBMC | 3/5 | 7 | PB |
| 5 | PBMC | 1/4 | 31 | BM, SP |
| 6 | ABM | 1/11 | 7 | PB |
| 7 | ABM | 1/14 | 7 | PB |
| 8 | ABM | 1/9 | 28 | BM |
| 9 | FBM | 1/4 | 30 | BM |
| 10 | FBM | 1/4 | 29 | BM |
| 11 | FBM | 1/4 | 29 | SP |
| 12 | FBM | 1/3 | 29 | BM |

Abbreviations: PB, peripheral blood; BM, bone marrow; SP, spleen; PBMC, peripheral blood mononuclear cells; ABM, adult bone marrow; FBM, fetal bone marrow.

What is claimed is:

1. A genetically immunodeficient rodent comprising exogenous cells, wherein the exogenous cells consist of human hematopoietic cells, wherein the peripheral blood of the immunodeficient rodent contains T-cells of human origin which is at least 20%.

2. The genetically immunodeficient rodent of claim 1, wherein the peripheral blood contains at least 30 % T-cells of human origin.

3. The genetically immunodeficient rodent of claim 1, wherein the peripheral blood contains at least 50% T-cells of human origin.

4. The rodent of claim 1, wherein the rodent is a mouse.

5. The rodent of claim 1, wherein the rodent is a beige/nude/xid mouse.

6. A method of making a rodent model for screening a substance for its effect on human T cells, consisting of:
   1) providing a genetically immunodeficient rodent;
   2) administering to the rodent a dose of radiation sufficient to establish at least 20% T-cells of human origin in the peripheral blood of the rodent upon transplantation of human peripheral blood mononuclear cells; and
   3) transplanting into the rodent an amount of human peripheral blood mononuclear cells sufficient to establish at least 20% T-cells of human origin in the peripheral blood of the rodent.

7. The method of claim 6, wherein the rodent is a mouse.

8. The method of claim 6, wherein the dose of radiation is equivalent to at least about 400 rads in a mouse.

9. The method of claim 6, wherein the dose of radiation is equivalent to between 400 and 1100 rads in a mouse.

10. The method of claim 6, wherein the number of cells transplanted is at least about 5×$10^8$ cells per kilogram of the rodent's body weight.

11. The method of claim 6 wherein the human cells are obtained by apheresis.

12. The method of claim 6, wherein the irradiation dose and transplantation amount are sufficient to establish at least 30% T-cells of human origin in the peripheral blood of the rodent.

13. The method of claim 6, wherein the irradiation dose and transplantation amount are sufficient to establish at least 50% T-cells of human origin in the peripheral blood of the rodent.

14. The method of claim 6, wherein the irradiation dose and transplantation amount are sufficient to establish at least 70% T-cells of human origin in the peripheral blood of the rodent.

15. A method of screening a substance for its effect on human T-cells, comprising:
1) obtaining a genetically immunodeficient rodent comprising exogenous cells, wherein the exogenous cells consist of human hematopoietic cells, wherein the peripheral blood of the immunodeficient rodent contains T-cells of human origin which is at least 20%;
2) administering a substance to the rodent; and
3) observing the effect of the substance on the human T-cells in the rodent.

16. The method of claim 15, wherein the peripheral blood of the genetically immunodeficient rodent contains at least 30% T-cells of human origin.

17. The method of claim 15, wherein the peripheral blood of the genetically immunodeficient rodent contains at least 50% T-cells of human origin.

18. The method of claim 15, wherein the peripheral blood of the genetically immunodeficient rodent contains at least 70% T-cells of human origin.

19. The method of claim 15, wherein the rodent is a mouse.

20. A genetically immunodeficient rodent comprising exogenous cells, wherein the exogenous cells consist of human hematopoietic cells, wherein the peripheral blood of the immunodeficient rodent contain T-cells of human origin which is at least 20%, in the absence of exogenous organ tissue or exogenous non-human hematopoietic cells.

21. The genetically immunodeficient rodent of claim 20, wherein the peripheral blood contains at least 30 % T-cells of human origin.

22. The genetically immunodeficient rodent of claim 20, wherein the peripheral blood contains at least 50% T-cells of human origin.

23. The rodent of claim 20, wherein the rodent is a mouse.

24. The rodent of claim 20, wherein the rodent is a beige/nude/xid mouse.

25. A method of making a rodent model for screening a substance for its effect on human T cells, consisting of:
1) providing a genetically immunodeficient rodent;
2) administering to the rodent a dose of radiation sufficient to establish at least 20% T-cells of human origin in the peripheral blood of the rodent upon transplantation of human peripheral blood mononuclear cells; and
3) transplanting into the rodent an amount of human peripheral blood mononuclear cells sufficient to establish at least 20% T-cells of human origin in the peripheral blood of the rodent, in the absence of exogenous organ tissue or exogenous non-human hematopoietic cells.

26. A method of screening a substance for its effect on human T-cells, comprising:
1) obtaining a genetically immunodeficient rodent comprising exogenous cells, wherein the exogenous cells consist of human hematopoietic cells, wherein the peripheral blood of the immunodeficient rodent contain T-cells of human origin which is at least 20%, in the absence of exogenous organ tissue or exogenous non-human hematopoietic cells,
2) administering a substance to the rodent; and
3) observing the effect of the substance on the human T-cells in the rodent.

27. The rodent of claim 1, wherein the percentage of human T cells is non-lethal.

* * * * *